United States Patent
Pagano Flores

(10) Patent No.: US 10,827,770 B2
(45) Date of Patent: Nov. 10, 2020

(54) PROCESS FOR PREPARING CONCENTRATED FOAMING COMPOSITIONS SWEETENED WITH HONEY AND SUCH COMPOSITIONS

(71) Applicant: Silvia Marina Pagano Flores, Barcelona (ES)

(72) Inventor: Silvia Marina Pagano Flores, Barcelona (ES)

(*) Notice: Subject to any disclaimer, the term of this patent is extended or adjusted under 35 U.S.C. 154(b) by 500 days.

(21) Appl. No.: 15/101,782

(22) PCT Filed: Dec. 3, 2014

(86) PCT No.: PCT/ES2014/070893
§ 371 (c)(1),
(2) Date: Jun. 3, 2016

(87) PCT Pub. No.: WO2015/082747
PCT Pub. Date: Jun. 11, 2015

(65) Prior Publication Data
US 2016/0309757 A1    Oct. 27, 2016

Related U.S. Application Data

(60) Provisional application No. 61/911,124, filed on Dec. 3, 2013.

(51) Int. Cl.
| | | |
|---|---|---|
| A23L 21/25 | (2016.01) | |
| A23P 30/40 | (2016.01) | |
| A23F 5/46 | (2006.01) | |
| A23C 9/152 | (2006.01) | |
| A23C 9/156 | (2006.01) | |
| A61K 35/644 | (2015.01) | |
| A23C 9/154 | (2006.01) | |
| A23G 3/52 | (2006.01) | |
| A23L 2/60 | (2006.01) | |
| A23L 29/20 | (2016.01) | |
| A23G 1/56 | (2006.01) | |
| A23L 27/00 | (2016.01) | |

(52) U.S. Cl.
CPC ............ *A23L 21/25* (2016.08); *A23C 9/156* (2013.01); *A23C 9/1524* (2013.01); *A23C 9/1544* (2013.01); *A23F 5/465* (2013.01); *A23G 1/56* (2013.01); *A23G 3/52* (2013.01); *A23L 2/60* (2013.01); *A23L 29/20* (2016.08); *A23P 30/40* (2016.08); *A61K 35/644* (2013.01); *A23C 2210/30* (2013.01); *A23L 27/00* (2016.08); *A23V 2002/00* (2013.01)

(58) Field of Classification Search
CPC ................................. A23L 21/25; A23P 30/40
USPC .......................................................... 426/569
See application file for complete search history.

(56) References Cited

U.S. PATENT DOCUMENTS

| | | | |
|---|---|---|---|
| 4,004,040 A | 1/1977 | Puta | |
| 4,478,867 A * | 10/1984 | Zobel | A23L 9/22 |
| | | | 426/565 |
| 4,849,240 A | 7/1989 | Giddey et al. | |
| 2003/0124243 A1* | 7/2003 | Cotten | A23G 3/0004 |
| | | | 426/660 |
| 2003/0129267 A1 | 7/2003 | Lawrence | |

FOREIGN PATENT DOCUMENTS

| | | | |
|---|---|---|---|
| AR | 041612 A1 | 5/2005 | |
| CN | 102028071 A | 4/2011 | |
| EP | 2548446 A2 | 1/2013 | |
| ES | 212322 A1 | 3/1955 | |
| ES | 2396009 A1 | 2/2013 | |
| WO | WO 2009/100497 A1 | 8/2009 | |
| WO | WO-2012020747 A1 * | 2/2012 | ............. G03F 7/405 |

* cited by examiner

*Primary Examiner* — Jyoti Chawla
(74) *Attorney, Agent, or Firm* — Osha Bergman Watanabe & Burton LLP

(57) ABSTRACT

A process for preparing a concentrated foaming composition sweetened with honey, including: a) provision and weighing the necessary quantities of raw materials to be used, b) putting pure honey in a mixer and subjecting the honey to beating from about 250 rpm to about 1500 rpm for about 5 to 30 minutes, c) adding at least one raw material selected from soluble coffee, powdered milk and honey to the mixed honey from step b) while it is being mixed, and d) once the desired consistency is achieved, divide the composition obtained in step c) into containers for distribution and marketing. Compositions for making foaming coffee sweetened with honey, foaming coffee with milk sweetened with honey and foaming milk sweetened with honey obtained by this process.

11 Claims, 7 Drawing Sheets

PROCESS FOR PREPARING CONCENTRATED FOAMING COMPOSITIONS SWEETENED WITH HONEY AND SUCH COMPOSITIONS

FIELD OF THE INVENTION

The present invention pertains to the field of the food industry, in particular it relates to those useful processes for preparing concentrated foaming compositions, preferably compositions of drinks sweetened with honey and such compositions.

The present invention is also related to the cosmetic, pharmaceutical, and biochemical industries where these compositions can be employed.

PREVIOUS ART

In the previous art there are various documents that refer to the use of coffee and honey together for different purposes.

The application US2003129267 (A1) discloses a Kona coffee and 100% pure honey based skin cleansing product that is applied as a facial mask and helps to smooth and soften the skin. This document is linked to the cosmetic industry and proposes the use of 2 raw materials: insoluble coffee beans and heated honey.

The document CN102028071 (A) refers to honey to which starch, dextrin, cellulose and other binders are added. The preparation thus obtained is dehydrated by food additives. It is combined with coffee, tea, and other flavoring substances. The end result is a solid drink At least 8 raw materials are used, including some food additives (binders, gelling agents or thickeners and flavoring substance). In the mixing process mechanical intervention is not mentioned, nor is the way in which the coffee is combined in the preparation, which at the end a solid drink is obtained. There is no concrete information about its consistency.

The publication AR041612 (A1) refers to a mix of pure honey with strawberry, pineapple, banana, green apple, orange, lemon, vanilla, coffee, chocolate and butter flavors. These are added in a greater or lesser degree according to the required flavor. This is mixed until a uniform mass is obtained. Here 2 raw materials are used and the result of the process is a uniform mass of flavored honey.

The document GT198400028 (A) discloses a product that can be whipped to form mousse. Here multiple raw materials are used, among those, some food additives. The process is relatively simple and the result thereof is a solid storable product that can be turned into mousse. The base of the product is fat, binder and emulsifier, and it contains sugar or another natural or artificial sweetener plus additional flavorings.

The application ES212322 (A1) refers to the preparation of coffee with liquid milk. The raw materials are mixed; namely whole natural cow or sheep's milk as a base, roasted natural coffee, sugar or honey, and salt. The mixture is then heated. To the thus obtained mass is added rennet and is fermented. The product is stirred until the curd is separated from the whey. Then, the solid mass is separated, dried and then taken to mature. The end result is a solid fermented product similar in consistency to semi-soft cheese. 5 raw materials are used in a very complex process: raw materials are subject to mixing, stirring, cooking, fermentation, drying, and maturation. The end result is a coffee with milk in a solid semi-soft block.

None of the documents mentioned provide for a manufacturing method to make concentrated foaming compositions, preferably compositions to make drinks in the form of a dense consistent and stable product, which is used to make coffee, coffee with milk, or foaming milk by adding preferably hot water, without the necessity of beating. Such concentrated compositions are stable and can be used to fill sandwich cookies, cakes, or chocolates.

SUMMARY OF THE PRESENT INVENTION

It is therefore the purpose of this application, a process to prepare concentrated foaming compositions sweetened with honey, that consists of:
a) provision and weighing the necessary quantities of raw materials to be used.
b) provision of pure honey in a mixer and whipped at about 250 rpm to 1,500 rpm for about 5 to 30 minutes.
c) adding at least one raw material selected from soluble coffee, powdered milk and honey to the mixed honey from step b) while it is being mixed, and
d) once the desired consistency is achieved, divide the composition obtained in step c) into containers for distribution and marketing.

Additionally, a stabilizer is incorporated together with the raw material in step c).

Still further, chocolate in the form of cocoa powder, spices, natural flavors, alcohol, or natural alcohol flavors are added after step c) while it is still being mixed.

Alternatively, the milk used may be condensed or evaporated.

Preferably, the stabilizer used in the compositions is natural.

Said stabilizer is selected from the group consisting of carob gum (gum from carob seeds) guar gum, tragacanth gum, Arabic gum, xanthan gum, karaya gum, tara gum, gellan gum, pectins, pectin, amidated pectin, cellulose, cellulose powder, microcrystalline cellulose, modified celluloses such as methylcellulose, ethylcellulose, carboxymethylcellulose, and mixtures thereof.

Moreover, the spices are ground and selected from the group consisting of: anise, saffron, cardamom, cinnamon, juniper, ginger, nutmeg, vanilla, and mixtures thereof.

Additionally, natural essences are selected from the group consisting of almond, hazelnut, orange, vanilla, and mixtures thereof.

Also, the alcohol or natural alcohol essences are selected from the group consisting of rum, vodka, whiskey, whiskey cream, limoncello, amaretto, gin, triple-sec (Cointreau), cognac, grappa, and mixtures thereof.

Another object of the present invention, a composition to prepare foaming coffee sweetened with honey obtained through the described process, consists of:
70% to 85% pure honey, and
10% to 30% soluble coffee,
where the % are expressed as weight to weight %.

Yet another objective of the present invention, a composition for preparing foaming coffee with milk sweetened with honey obtained by the described process, consists of:
70% to 85% pure honey,
10% to 25% soluble coffee, and
5% to 15% powdered milk,
where the % are expressed as weight to weight %.

Yet another objective of the present invention, a composition for preparing foaming milk sweetened with honey obtained by the described process, consists of:

70% to 85% pure honey,
15% to 30% powdered milk,
where the % are expressed as weight to weight %.

The described compositions also have a stabilizer.

Still further, the composition consists of chocolate in the form of cocoa powder, spices, natural essences, alcohol, or natural alcohol essences, and mixtures thereof.

Alternatively, the milk can be condensed or evaporated.

Preferably, the stabilizer present in the compositions is natural.

The stabilizer is selected from the group consisting of carob gum (gum from carob seeds) guar gum, tragacanth gum, Arabic gum, xanthan gum, karaya gum, tara gum, gellan gum, pectins, pectin, amidated pectin, cellulose, cellulose powder, microcrystalline cellulose, modified celluloses such as methylcellulose, ethlycellulose, carboxymethylcellulose, carboxyethylcellulose, hydroxyprpylcellulose, hydroxypropylmethylcellulose, ethyl methylcellulose, and mixtures thereof.

Moreover, the spices are ground and selected from the group consisting of: anise, saffron, cardamom, cinnamon, juniper, ginger, nutmeg, vanilla, cloves, and mixtures thereof.

Additionally, natural essences are selected from the group consisting of almond, hazelnut, orange, vanilla, and mixtures thereof.

Also, the alcohol or natural alcohol flavor essences of are selected from the group consisting of rum, whiskey, whiskey cream, vodka, limoncello, amaretto, gin, triple-sec (Cointreau), cognac, grappa, and mixtures thereof.

Preferably, the stabilizer is present from 0.1% to 3% per weight of the composition.

Also preferably, the spices are present from 0.1% to 1.5% per weight of the composition.

In its preferred that the natural essences be present from 0.01% to 0.05% per weight of the composition.

Also in its preferred form, the alcohol, or natural alcohol flavor essences of are present from 0.01% to 0.5% per weight of the composition.

Meanwhile, the chocolate in form of cocoa powder is present from 1% to 3% per weight of the composition.

The condensed or evaporated milk is present from 2.5% to 8% per weight of the composition.

The shelf life of the compositions ranges from at least 6 months to approximately two years.

Lastly, the described compositions are for obtaining foaming coffee sweetened with honey or foaming coffee with milk sweetened with honey, or for foaming milk sweetened with honey by adding hot water.

DETAILED DESCRIPTION OF THE INVENTION

Figure 1:
FIG. 1 shows the inside of the mixer with the whipping accessory in contact with concentrated composition of foaming coffee sweetened with honey. This mixer is used to put into practice the process of the present invention.
Figure 2:
FIG. 2 shows the appearance of a concentrated composition of foaming coffee sweetened with honey in a jar, obtained by the process according to the preferred aspect of the present invention.
Figure 3:
FIG. 3 shows the dense and stable consistency of the concentrated composition of foaming coffee sweetened with honey of FIG. 2 prepared by the process according to the preferred aspect of the present invention.
Figure 4:
FIG. 4 shows a cup of coffee with foam prepared with a concentrated composition of foaming coffee sweetened with honey (Composition 1.a) obtained according to the preferred method of the process of the present invention without additives or stabilizers.
Figure 5:
FIG. 5 shows a cup of coffee with foam prepared with a concentrated composition of foaming coffee sweetened with honey (Composition 4) obtained according to the preferred method of the process of the present invention with a natural stabilizer.
Figure 6:
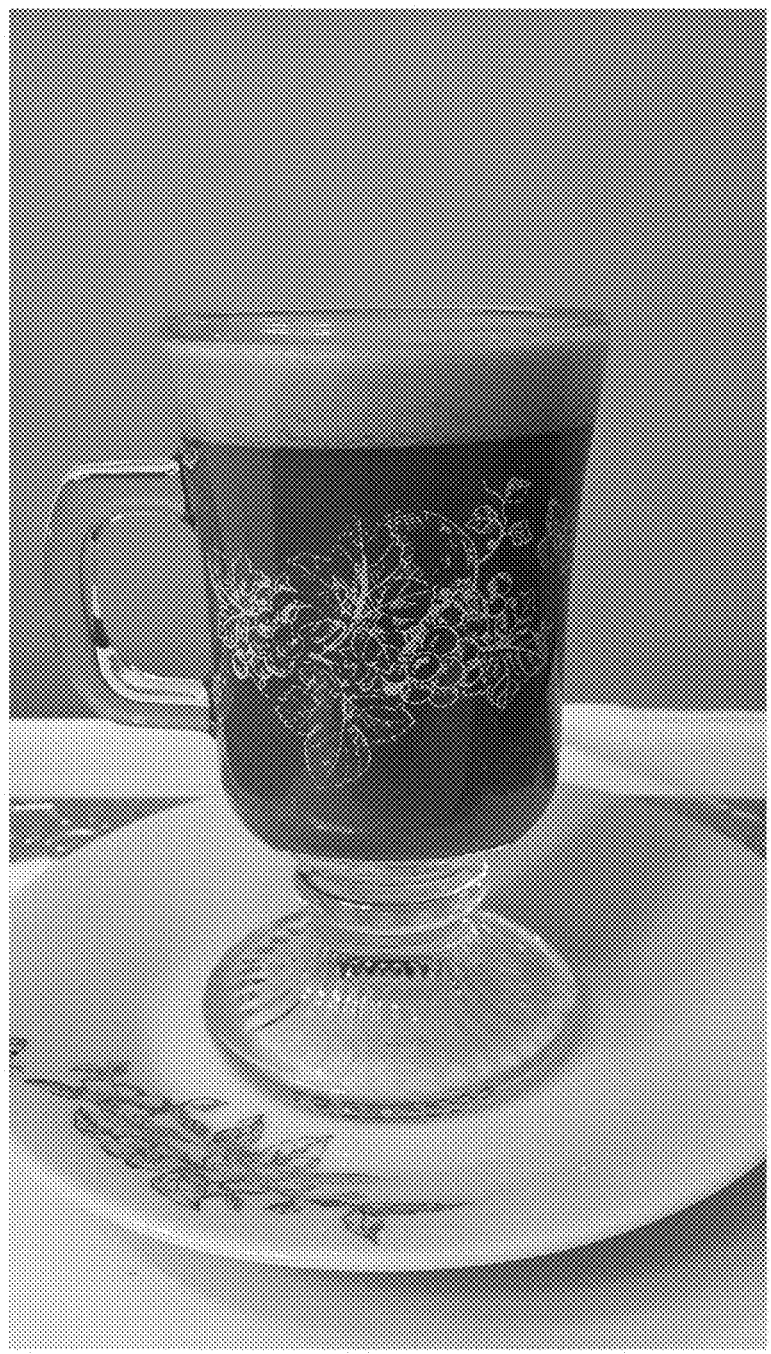
FIG. 6 shows a cup of coffee with milk with foam prepared with a concentrated composition of foaming coffee sweetened with honey (Composition 5) obtained according to the preferred method of the process of the present invention with a natural stabilizer.
Figure 7:
FIG. 7 shows a cup of milk with foam prepared with a concentrated composition of foaming coffee sweetened with honey (Composition 20) obtained according to the preferred method of the process of the present invention with a natural stabilizer.

The present invention consists of the manufacturing method for a new food product preferably with a base of coffee and/or milk sweetened with honey. It is healthier, foaming, instant, of practical usage, and has multiple applications.

The particular characteristics of this product effectually permit it to be used mainly in the food industry, making it possible to utilize it for various purposes and applications in other categories of the same industry.

This product can also be used as a base for use in other industries such as cosmetics, pharmaceuticals, and biochemistry.

The innovative and inventive activity characteristics of the manufacturing process of the products described here, concentrated foaming compositions, preferably compositions to prepare, coffee, coffee with milk, and foaming milk sweetened with honey, respond to two surprising effects obtained unexpectedly during the implementation of this process:

a) the unexpected capacity for honey to contain and maintain the air bubbles incorporated during this process for a long time, transforming the raw materials used in the concentrated foaming composition; and b) the yield of the final products obtained show an increase of between 40% and 70% in the original volume of the raw materials used.

It is known in the art that the bubbles formed during the handling of honey, one of the raw materials used as a principal material base here, are eliminated, when the honey is left to rest for the necessary time. The present bubbles gradually move within the mass of honey until they reach the surface and are eliminated.

During the manufacturing process here described, a great quantity of bubbles are incorporated in such a way that said displacement is stopped in such a way that they do not move within the mass of the final product, and are not eliminated. This makes the product stable enough to give it a shelf life of at least six months up to around 2 years, or more, preferably on the order of a year to a year and a half. In this way, the product can be conserved maintaining its properties, principally that of providing foam by adding water, preferably hot or very hot, without the necessity of whipping, which is common for these types of preparations. The foam achieved in this way is stable and consistent, providing a practically instant beverage.

The processes for handling honey described below show demonstrably that since prior to 1959 up to the present day, have not changed, and because of that, honey has been processed and marketed in basically three ways: filtered/liquid, crystallized/solid, and creamy.

Comparison between traditional processes and the mentioned ways of marketing honey regarding the proposed procedure here for the production of concentrated foaming compositions sweetened with honey, and such compositions can highlight two fundamental distinctive observations.

a) As for the presence of air bubbles:

Both producers and processors have worked and are working with honey nowadays with some incorporation of technology to a greater or lesser degree, or completely without, but the process always ends with a last or second to last stage of decantation or second filtration in decanter tanks in maturation holdings.

Decanting is carried out for a period of time ranging from 2 or 3 days to a month or more. This is considered necessary since with this the density of the air bubbles hidden in the honey are eliminated, along with impurities that were left from previous stages.

It's true that honey has the distinctive characteristic of "containing" hidden air bubbles in it during its handling, which can be removed by decantation. This means that with adequate resting time, the bubbles rise to the surface, break and disappear, but that they can not be "maintained." That is, honey can not accommodate these bubbles without them being altered or disappearing during the resting stage. This quality is modified by way of preparing and presenting "foam," which can be achieved through the application of a preferred way of preparing the product process here proposed.

b) As for the type or form of preparation and commercial presentation of the obtained by the product process applied by this here proposed:

The usual way that honey products are presented on the market are as "liquid or filtered honey," "creamy honey," or "crystallized honey."

To this day, a honey processed in the production process like the one of the present invention here proposed has not been presented. This process combines raw materials in concentrated foaming compositions. This product thus elaborated ceases to have the typical physical-chemical composition of honey, to become new foaming compositions which is a sine qua non that air bubbles are incorporated by intense whipping.

Therefore, the application of this procedure as detailed below, not covered so far, results in a stable product in a new commercial presentation of honey as "foaming." This gives the honey presented in this way the quality of maintaining and containing the air bubbles incorporated in the long term, giving it the particular characteristic of transforming into a "foaming" product which is instant, creamy, and of practical usage.

Obtaining a versatile product based on natural ingredients was sought for the following reasons:

1) For its beneficial health implications. The main objective is to offer the consumer a food product developed and sweetened with excellent raw materials: pure honey with unique characteristics which make it naturally healthier; soluble coffee, preferably unroasted, powdered milk, or a mix of both. This objective justifies further application in multiple categories of the food industry.

By "pure honey" we refer to the sweet and viscous fluid produced by honey bees as their main product. They make this from nectar collected mainly from flowers. Being a natural product, it is free from contaminants and/or additives of any kind. The bees collect, transform and combine the nectar with the invertase enzyme contained in their saliva. They then store it in the honeycombs where it matures, transforming it from a thin and perishable liquid substance to a stable high-carbohydrate substance. The physical chemical and organoleptic properties of honey are determined by the type of nectar the bees collect. The botanical origin of the plants used for honey also make it harder or easier to crystallize.

By "soluble" or instantaneous coffee, we refer to a product obtained by a process in which the soluble solids are extracted from the roasted and ground coffee by an operation of solid-liquid extraction. The solvent water is partially evaporated and the subsequently removed using a drying spray (the extract is atomized in a drying chamber where it is put into contact with hot air) or lyophilization (the extract is frozen at low temperatures and is later submerged in water at low pressure) to achieve a powdered or granulated product capable of rapidly dissolving in water for consumption.

By "powdered milk" or dehydrated milk we refer to the product obtained by dehydrating pasteurized milk. This is done in atomization towers where the water present in the milk is evaporated, obtaining a yellowish white powder which contains the natural properties of the milk. To turn it into a liquid state before drinking it, the powder should be dissolved in drinking water. This product is important because it does not have to kept cold, elongating its shelf life.

By "natural stabilizer" we refer to any accepted and commonly used product used as a stabilizer in the food industry. It is from a natural source, or at least comes from a natural source and was chemically or enzymatically modified. With this clarification, it should be understood that "stabilizer" and "natural stabilizer" are used interchangeably here. However for the purposes of the present invention those stabilizers which are naturally occurring without chemical modifications of any kind are preferred. The person skilled in the art will perfectly know how to distinguish one from another considering this definition. The stabilizer provides stability for the foam and stability against temperature changes that the product could be exposed to. Without intending this to be considered limiting, and any stabilizer can be used, the preferred stabilizers are in the group consisting of carob gum (gum from carob seeds) guar gum, tragacanth gum, Arabic gum, xanthan gum, karaya gum, tara gum, gellan gum, pectins, pectin, amidated pectin, cellulose, cellulose powder, microcrystalline cellulose, modified celluloses such as methylcellulose, ethlycellulose, carboxymethylcellulose, carboxyethylcellulose, hydroxypropylcellulose, hydroxypropylmethylcellulose, ethyl methylcellulose, and mixtures thereof, 2) For the exclusive characteristics of raw honey. The product obtained by the process of the present invention is specially made with pure honey. An identical or similar product with these singular characteristics and health benefits could not be achieved if it were replaced by any other sweetener. For example, any honey that is diluted or adulterated with other products that are not bee products, such as any kind of sugar would not be acceptable.

3) It allows the consumer to taste a product that, because of its manufacturing process is already sweetened, at its ideal point. It has foam without requiring this to be done manually and separately. Also, because of its particular characteristics in its consistency, it is of practical usage and allows for multiple applications.

Therefore, the object of the present invention is a process for the manufacturing of a concentrated foaming composition sweetened with honey to prepare coffee, late, or foamy milk, ready to consume and for the products obtained in the same way. The obtained compositions are coffee or milk based food products sweetened with honey, healthier, foaming, of instant preparation, of practical usage, and with multiple applications.

The first stage of manufacturing of the food products of the present invention, compositions to prepare coffee, coffee with milk, and foaming milk sweetened with honey, consists of the selection of the raw materials, that in its base formula, are pure honey, soluble coffee and/or powdered milk.

For example, the preparation of a concentrated coffee, coffee with milk, or foaming milk composition requires the application of a production process that involves:

a) Selecting the materials and raw materials needed, and dividing their proportions according to the variables to prepare, according to the components and parameters established in the section corresponding to the formulations.

b) Placing the raw materials in a properly conditioned container to start the production process. It should be noted that, given the yield you get from this product, the containers used should hold approximately at least 50% more volume to contain the increase in volume generated in the process.

c) Submitting the honey with the soluble coffee, powdered milk, or soluble coffee and powdered milk to a process of mechanical mixing and aerating. This is the same whether or not other ingredients are added.

d) This production process should be applied to the raw materials, in proportions indicated in the corresponding composition, at a beating power of medium/high for the raw materials to be whipped and aerated with a beater from about 250 rpm to 1,500 rpm, and for 5 to 30 minutes. That is, for enough time to obtain a desired consistency as to achieve a shelf life on the order of at least about six months to about two years.

During the whipping of the raw materials of the composition to be prepared, the product should not exceed 35° C., and more preferably 30° C. And during the dividing and packaging process, the obtained product should be in the best state between approximately 24° C. and 27° C.

Thus, the mentioned raw materials are transformed, becoming a new product: a concentrated foaming composition, airy, and creamy, of a consistency highly superior to mousse. It can be used to make foamy honey sweetened coffee, foamy honey sweetened coffee with milk, or foamy honey sweetened milk by adding hot water.

e) For example, with the application of the production process, a quantity of 1 kg of raw material, whipped for a period indicated in point (d), an incremental yield of between 40% and 70% compared to the original volume of the raw materials used is achieved. That is, approximately 1,400 $cm^3$ to 1,700 $cm^3$ of a concentrated foaming final product.

The principal process variables of the process, rpm, and stirring time can be selected according to the characteristics of the desired final product, the machinery used, and the volume of the mixture of the raw materials used. In this way, and according to circumstances, more rpm needs less time to achieve the same result achieved with less rpm and more stirring or beating time.

The concentrated foaming composition to prepare foaming coffee sweetened with honey or coffee with foaming milk sweetened with honey, or foaming milk sweetened with honey obtained with the process proposed here is not as yet typified in the Argentine Food Code, or in other equivalents documents of the same or similar importance with specific name that identifies it.

Nor was it found in the various markets that sell food products of this type, any identical or similar products.

The name foaming coffee, foaming coffee with milk, or foaming milk is directly related to 2 important considerations:

1) To the particular mechanical whipping and aeration process applied to the combination of raw materials used according to the type of product. The process makes it possible to obtain the composition for preparing foaming coffee sweetened with honey or coffee with foaming milk sweetened with honey, or for foaming milk sweetened with honey by providing such a quantity of air bubbles that they transform the utilized raw materials into a new product, with a base of coffee, coffee with milk, or foaming and aerated milk, with a consistency far superior to mousse, since the bubbles are contained and maintain in the product in the long term, from around approximately 6 months to 24 months, without it suffering alterations over time. Additionally, it preserves a delicate balance between the taste and body of the coffee, milk or mixture of the two, with the sweet aroma of the honey.

2) The air bubbles formed at the time of preparing the composition to prepare the foaming coffee sweetened with honey or coffee with foaming milk sweetened with honey, or for foaming milk sweetened with honey are distributed throughout the product evenly. They do not bind together or get lost. Thus, once prepared, only some of the bubbles, those that are in contact with the interior of the container, rise slowly to the surface, without changing the consistency of the end result in the interior of the composition to prepare foaming coffee sweetened with honey or coffee with foaming milk sweetened with honey, or for foaming milk sweetened with honey, just like the bubbles in fine sparkling wines do. Approximately not less than about 95% of the bubbles are contained and maintained thanks to the transformation undertaken by the raw materials used, generated with the application of the production process described here before.

Raw Materials Used According to Type of Composition:
According to the Formula Base and Variants The composition to prepare a foaming coffee sweetened with honey may be presented with, but is not limited to, the following varieties of flavors, although they:

Original flavor (coffee and honey) with or without natural stabilizer

With cinnamon (coffee, honey, and cinnamon)

With cinnamon and chocolate (coffee, honey, cinnamon, and chocolate)

With spices (various ground spices, such as anise, saffron, cardamom, cinnamon, juniper, ginger, nutmeg, vanilla, cloves, etc.)

With powdered milk

With condensed or evaporated milk

With alcohol or natural essences or different alcohol flavors (such as rum, whiskey, whiskey cream, vodka, limoncello, gin, coffee liqueur, créme de cacao, amaretto, triple-sec (Cointreau), cognac, grappa, etc.)

With natural essences of different flavors (almond, hazelnut, orange, vanilla, etc.)

EXAMPLES OF COMPOSITIONS

The following compositions are examples of how to best implement the present invention, but should not be considered limiting. Thus, variants of these compositions should be considered as falling within the scope of the present invention.

COMPOSITION 1: This is a composition for preparing foaming coffee sweetened with honey or original flavor foaming honey coffee of mild or strong intensity.

The original formula also supports all flavors that are formulated with a natural stabilizer.

a) Mild Intensity:

| COMPONENT | % w/w |
|---|---|
| Pure honey | 83.5 |
| Soluble coffee | 16.5 | b) Strong Intensity:

| COMPONENT | % w/w |
|---|---|
| Pure honey | 75.2 |
| Soluble coffee | 24.8 |

COMPOSITION 2: Composition for preparing foaming coffee sweetened with honey with at least one natural stabilizer.

| COMPONENT | % w/w |
|---|---|
| Pure honey | 81.50% |
| Soluble coffee | 16.50% |
| Natural stabilizer | 2.00% |

The natural stabilizer used is microcrystalline cellulose (Avicel, Avicel-plus, NovaGel).

The "microcrystalline cellulose" E-461 (i) or MCC (English acronym for Microcrystalline Cellulose) is a partially depolymerised purified cellulose, obtained by treatment with mineral acids of the alpha-cellulose in vegetable fibers.

COMPOSITION 3: Composition for preparing foaming coffee sweetened with spiced honey.

| COMPONENT | % w/w |
|---|---|
| Pure honey | 81.5 |
| Soluble coffee | 15.5 |
| Natural stabilizer | 2 |
| Spices | 1 |

The natural stabilizer employed is microcrystalline cellulose (MCC) and the spices are selected from anise, saffron, cardamom, cinnamon, juniper, ginger, nutmeg, vanilla, cloves, and mixtures thereof. In this case, anise and juniper were used in equal parts COMPOSITION 4: Composition for preparing foaming coffee sweetened with honey with the addition of cinnamon and chocolate.

| COMPONENT | % w/w |
|---|---|
| Pure honey | 81.5 |
| Soluble coffee | 14 |
| Natural stabilizer | 2 |
| Spices | 1 |
| Chocolate (cocoa powder) | 1.5 |

The natural stabilizer is microcrystalline cellulose (MCC). In addition to the cinnamon used here, other spices can be added in varying proportions depending on the result sought to achieve in the taste of the final product, where such spices are selected from anise, saffron, cardamom, juniper, ginger, nutmeg, vanilla, cloves, and mixtures thereof.

COMPOSITION 5: Composition to prepare foaming coffee with milk sweetened with honey made with powdered milk.

| COMPONENT | % w/w |
|---|---|
| Pure honey | 71.5 |
| Soluble coffee | 16.5 |
| Natural stabilizer | 2 |
| Powdered milk | 10 |

The natural stabilizer is microcrystalline cellulose (MCC).

COMPOSITION 6: Composition to prepare foaming coffee with milk sweetened with honey made with condensed milk.

| COMPONENT | % w/w |
|---|---|
| Pure honey | 71.5 |
| Soluble coffee | 21.5 |
| Natural stabilizer | 2 |
| Condensed milk | 5 |

The Natural stabilizer is carboxymethylcellulose.

The "carboxymethylcellulose" E-466 or CMC (Carboxymethyl Cellulose English acronym) is a cellulose derivative comprised of carboxymethyl groups bonded to hydroxyl present in some groups of glucopyranose polymers.

COMPOSITION 7: Composition for preparing foaming coffee sweetened with honey with natural essences.

| COMPONENT | % w/w |
|---|---|
| Pure honey | 81.49 |
| Soluble coffee | 16.5 |
| Natural stabilizer | 2 |
| Natural essences | 0.01 |

The natural stabilizer is microcrystalline cellulose (MCC). The Natural essences are selected from almond, hazelnut, orange, vanilla, and mixtures thereof. In this case orange essence was used.

COMPOSITION 8: Composition for preparing foaming coffee sweetened with honey with at least one natural stabilizer.

| COMPONENT | % w/w |
|---|---|
| Pure honey | 81.5 |
| Soluble coffee | 16.5 |
| Natural stabilizer | 2 |

The natural stabilizer was locust bean gum.

"Locust bean gum" is also known as carob bean gum or E410, it is a type of galactomannan vegetable gum extracted from the seeds of the carob tree. The fruit of the carob tree is used to prepare the rubber that is used as a stabilizer COMPOSITION 9: Composition for preparing foaming coffee sweetened with spiced honey.

| COMPONENT | % w/w |
|---|---|
| Pure honey | 83 |
| Soluble coffee | 15.5 |
| Natural stabilizer | 0.5 |
| Spices | 1 |

The natural stabilizer is locust bean gum. The spices are selected from anise, saffron, cardamom, cinnamon, juniper, ginger, nutmeg, vanilla, cloves, and their mixtures in varying proportions depending on the flavor you want to achieve. In this case weight equal parts of vanilla, juniper, anise and cardamom was used.

COMPOSITION 10: Composition for preparing foaming coffee sweetened with honey with the addition of cinnamon and chocolate.

| COMPONENT | % w/w |
|---|---|
| Pure honey | 82.5 |
| Soluble coffee | 14.5 |
| Natural stabilizer | 0.1 |
| Spices | 1.3 |
| Chocolate (cocoa powder) | 1.6 |

The natural stabilizer is locust bean gum. In addition to cinnamon as was used in this example, other spices can be added in varying proportions depending on the result in the flavor that is intended to achieve, where these spices are selected from anise, saffron, cardamom, juniper, ginger, nutmeg, vanilla, cloves, and mixtures thereof.

COMPOSITION 11: Composition to prepare foaming coffee with milk sweetened with honey made with powdered milk.

| COMPONENT | % w/w |
|---|---|
| Pure honey | 72 |
| Soluble coffee | 16.5 |
| Natural stabilizer | 1.5 |
| Powdered milk | 10 |

The natural stabilizer es carob gum.

COMPOSITION 12: Composition to prepare foaming coffee with milk sweetened with honey made with condensed milk.

| COMPONENT | % w/w |
|---|---|
| Pure honey | 73 |
| Soluble coffee | 21.5 |
| Natural stabilizer | 0.5 |
| Condensed milk | 5 |

The natural stabilizer es carob gum.

"Condensed milk" is basically cow's milk from which the water has been extracted and sugar added has been added, yielding a thick and sweet product. It is preserved for a long time without refrigeration as long as the package remains sealed. Alternatively, it is preferred to employ "evaporated milk" which is a canned milk product that also supports large storage periods due to the dehydration process performed on the raw milk, whereby it eliminates about 60% of the water existing in milk. The latter product is preferred due to the fact that the compositions obtained would be sweetened only with honey.

COMPOSITION 13: Composition for preparing foaming coffee sweetened with honey with natural essences.

| COMPONENT | % w/w |
|---|---|
| Pure honey | 81.49 |
| Soluble coffee | 16.5 |
| Natural stabilizer | 2 |
| Natural essences | 0.01 |

The natural stabilizer is carob gum and the natural essences are selected from almond, hazelnut, orange, vanilla, and mixtures thereof. In this case, equal parts of hazelnut and orange were used.

COMPOSITION 14: Composition for preparing foaming coffee sweetened with honey with at least one natural stabilizer.

| COMPONENT | % w/w |
|---|---|
| Pure honey | 81.5 |
| Soluble coffee | 16.5 |
| Natural stabilizer | 2 |

The natural stabilizer is xanthan gum.

"Xanthan gum" or simply "Xanthan" refers to an extracellular polysaccharide produced by the bacterium *Xanthomonas campestris*. It is a cream colored powder that dissolves in hot or cold water to produce solutions of relatively high viscosity at low concentrations, hence its use as a thickener.

COMPOSITION 15: Composition for preparing foaming coffee sweetened with spiced honey.

| COMPONENT | % w/w |
|---|---|
| Pure honey | 81.5 |
| Natural stabilizer | 1 |
| Soluble coffee | 16.5 |
| Spices | 1 |

The natural stabilizer is xanthan gum. The spices are selected from anise, saffron, cardamom, cinnamon, juniper, ginger, nutmeg, vanilla, cloves, and mixtures thereof. In this case equal parts cardamom, vanilla and ginger were used.

COMPOSITION 16: Composition for preparing foaming coffee sweetened with honey with the addition of cinnamon and chocolate.

| COMPONENT | % w/w |
|---|---|
| Pure honey | 81.4 |
| Soluble coffee | 16 |
| Natural stabilizer | 0.1 |
| Spices | 1 |
| Chocolate (cacao powder) | 1.5 |

The natural stabilizer is xanthan gum. In addition to the cinnamon as used here, other spices can be added in varying proportions depending on the result in the flavor that is intended to achieve, where these spices are selected from anise, saffron, cardamom, juniper, ginger, nutmeg, vanilla, cloves odor, and mixtures thereof.

COMPOSITION 17: Composition for preparing foaming coffee with milk sweetened with honey made with powdered milk

| COMPONENT | % w/w |
| --- | --- |
| Pure honey | 73.3 |
| Soluble coffee | 16.5 |
| Natural stabilizer | 0.2 |
| Powdered milk | 10 |

The natural stabilizer is xanthan gum.

COMPOSITION 18: Composition for preparing foaming coffee with milk sweetened with honey using condensed milk.

| COMPONENT | % w/w |
| --- | --- |
| Pure honey | 73 |
| Soluble coffee | 21.5 |
| Natural stabilizer | 0.5 |
| Condensed milk | 5 |

The natural stabilizer is xanthan gum.

COMPOSITION 19: Composition for preparing foaming coffee sweetened with honey with natural essences.

| COMPONENT | % w/w |
| --- | --- |
| Pure honey | 81.49 |
| Soluble coffee | 17 |
| Natural stabilizer | 1.5 |
| Natural essences | 0.01 |

The natural stabilizer is xanthan gum. The natural essences are selected from almond, hazelnut, orange, vanilla, and mixtures thereof. In this Example natural almond essence was used.

COMPOSITION 20: Composition for preparing foaming milk sweetened with honey.

| COMPONENT | % w/w |
| --- | --- |
| Pure honey | 82.5 |
| Powdered milk | 15.5 |
| Natural stabilizer | 2 |

The natural stabilizer is microcrystalline cellulose (MCC).

COMPOSITION 21: Composition for preparing foaming milk sweetened with honey with added cinnamon.

| COMPONENT | % w/w |
| --- | --- |
| Pure honey | 83 |
| Powdered milk | 14.5 |
| Natural stabilizer | 2 |
| Spices | 0.5 |

The natural stabilizer is xanthan gum. In addition to the cinnamon as used here, you can add other spices in varying proportions depending on the result in the flavor that is intended to achieve, the spices are selected from anise, saffron, cardamom, juniper, ginger, nutmeg, vanilla, cloves odor, and mixtures thereof.

Product Stability

The trial performed were of accelerated stability; which establish a period of shelf We and determine the stability of the foam of the formulated product.

Jars with the compositions were placed for 25 days at different temperatures: oven at 35° C., oven at 25° C., room temperature, refrigerator at 7° C. and refrigerator at 2° C.

After that period of time passed, a visual assessment of each composition and its ability to produce a beverage by adding hot water to the desired characteristics was performed.

Slight variations at 35° C. were seen in the packaging of the compositions prepared without stabilizer. A small separation of form was detected where about 3 to 4 mm of the coffee is darker at the bottom of the product. Products made with various stabilizers were unchanged in appearance for any of the temperatures of the trials.

It is concluded that to obtain a commercially acceptable product for a period of up to two years it is convenient to use stabilizers.

The compositions without stabilizers may have a shelf life of between one year and one and a half years.

Foam Stability

Tests were done to make the final beverage to be consumed by the addition of hot drinking water at a temperature between 80 and 98° C. from a height of about 15 cm on each of the compositions coffee, coffee with milk, and milk sweetened with honey prepared according to the present invention process and described above.

We waited for about 35 seconds after mixing, resulting in foam that had a height between about 0.8 cm and about 2.3 cm, which remained until the ready to consume product was cooled to room temperature.

The foam on the beverages obtained with compositions without stabilizer had a foam height development lower than those of beverages obtained from the compositions with a stabilizer.

The products made with various stabilizers presented no change in appearance or in foaming abilities in the trials at the mentioned temperatures.

Uses and Applications of the Concentrated Foaming Compositions:

Food Industry

The composition for preparing foaming coffee sweetened with honey has the following applications in the food industry, classified by category:

α) Hot drinks:
Foaming Coffee.
Foaming Coffee with milk (powdered or condensed)
Foaming Spiced Coffee—alone or with milk—
Foaming Coffee with Chocolate and Cinnamon—Cappuccino—
Foaming Coffee flavored with Natural essences/Liqueurs β) Bonbons:
Filling for bonbons χ) Confectionery:
Filling for nougat
Filling for sandwich cookies
Filling for sweets
Filling for cookies δ) Pastry:
Filling for baked goods: cookies, cakes, jelly rolls, etc.

ε) Ice Cream:
Flavor base, cover or filling for ice cream or frozen desserts

Cosmetic Industry

As a base for the preparation of skin care creams, soap bars, liquid soaps, foams and/or bath salts, lip balms, etc.

Pharmaceutical and Biochemical Industry

As a base for granulated or effervescent painkillers, fever reducers, and also for the production of syrups.

The invention claimed is:

1. A process for preparing a concentrated foaming composition sweetened with honey, comprising:
    (a) placing pure honey in a mixer and subjecting the honey to whipping with a beater from about 250 rpm to about 1500 rpm for about 5 to 30 minutes,
    (b) adding at least one raw material selected from soluble coffee and powdered milk to the honey from step (a) while the honey is being whipped, to form a composition, and
    (c) continuing the whipping until a stable consistency of the composition is achieved, then dividing the composition obtained in step (b) into containers for distribution and marketing,
    wherein the temperature of the honey during whipping does not exceed 35° C., and
    wherein the consistency of the divided composition is such that at least 95% of bubbles resulting from the whipping and aerating are maintained in the divided composition for a shelf-life of at least 6 months.

2. The process of claim 1, further comprising adding a stabilizer in addition to the raw materials of step (b).

3. The process of claim 1, further comprising adding at least one of:
    chocolate in the form of cocoa powder, spices, natural flavors, natural essences, alcohol or alcohol flavors, and mixtures thereof after step (b) while the composition is still being whipped.

4. The process of claim 3, wherein the spices are ground and selected from the group consisting of anise, saffron, cardamom, cinnamon, juniper, ginger, nutmeg, vanilla, clove, and mixtures thereof.

5. The process of claim 3, wherein the natural essences are selected from the group consisting of almond, hazelnut, orange, vanilla, and mixtures thereof.

6. The process of claim 3, wherein the alcohol or alcohol flavors are selected from the group consisting of rum, whiskey, whiskey cream, vodka, limoncello, amaretto, gin, coffee liqueur, cocoa cream, amaretto, triple-sec, cognac, grappa, and mixtures thereof.

7. The process of claim 1, wherein the powdered milk is evaporated milk.

8. A process for preparing a concentrated foaming composition sweetened with honey, comprising:
    (a) placing pure honey in a mixer and subjecting the honey to whipping and aerating with a beater from about 250 rpm to about 1500 rpm for about 5 to 30 minutes;
    (b) adding at least one raw material selected from soluble coffee and powdered milk to the honey from step (a) while the honey is being whipped and aerated, to form a composition; and
    (c) continuing the whipping and aerating until a volume of the composition is 40% to 70% greater than a combined un-whipped volume of the pure honey and the at least one raw material is achieved;
    (d) dividing the composition obtained in step (c) into containers for distribution and marketing;
    wherein the temperature of the honey during whipping and aerating steps (a)-(c) and dividing step (d) does not exceed 35° C.

9. The process of claim 8, wherein the temperature of the honey during whipping steps (a)-(c) and dividing step (d) does not exceed 30° C.

10. The process of claim 8, wherein a consistency of the divided composition is such that at least 95% of bubbles resulting from the whipping and aerating are maintained in the divided composition for a shelf-life of at least 6 months.

11. The process of claim 8, wherein a consistency of the divided composition is such that at least 95% of bubbles resulting from the whipping and aerating are maintained in the divided composition for a shelf-life of at least 12 months.

* * * * *